(12) United States Patent
Miyachi

(10) Patent No.: US 11,103,218 B2
(45) Date of Patent: Aug. 31, 2021

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 593 days.

(21) Appl. No.: 15/967,853

(22) Filed: May 1, 2018

(65) Prior Publication Data

US 2018/0242954 A1   Aug. 30, 2018

Related U.S. Application Data

(63) Continuation of application No. PCT/JP2016/081733, filed on Oct. 26, 2016.

(30) Foreign Application Priority Data

Nov. 2, 2015 (JP) .............................. JP2015-215611

(51) Int. Cl.
  *A61B 8/08* (2006.01)
  *G01S 15/89* (2006.01)
  (Continued)

(52) U.S. Cl.
  CPC .............. *A61B 8/5276* (2013.01); *A61B 8/14* (2013.01); *A61B 8/485* (2013.01); *A61B 8/54* (2013.01);
  (Continued)

(58) Field of Classification Search
  CPC ......... A61B 8/5276; A61B 8/485; A61B 8/14; A61B 8/54; A61B 8/08; G01S 15/8986;
  (Continued)

(56) References Cited

U.S. PATENT DOCUMENTS

| 4,955,386 A * | 9/1990 | Nishiyama | G01P 5/244 |
| | | | 600/455 |
| 2001/0034485 A1* | 10/2001 | Kawagishi | G01S 7/52026 |
| | | | 600/443 |
| 2007/0213614 A1* | 9/2007 | Suzuki | G01S 7/52026 |
| | | | 600/443 |

FOREIGN PATENT DOCUMENTS

| JP | 5-200024 A | 8/1993 |
| JP | 7-51270 A | 2/1995 |

(Continued)

OTHER PUBLICATIONS

Hasegawa et al. 2002 Jpn. J. Appl. Phys. 41:3563-3571 (Year: 2002).*

(Continued)

*Primary Examiner* — Michael J Tsai
*Assistant Examiner* — Patrick M Mehl
(74) *Attorney, Agent, or Firm* — Birch, Stewart, Kolasch & Birch, LLP.

(57) ABSTRACT

An ultrasound diagnostic apparatus includes: an ultrasound probe; a transmission and reception unit that transmits an ultrasound beam from the ultrasound probe toward a subject, receives an ultrasound beam reflected from the subject, and processes a received signal output from the ultrasound probe to generate received data; a complex data generation unit that generates first complex data including amplitude information and phase information by orthogonally detecting the received data generated by the transmission and reception unit using a first center frequency and a first cutoff frequency and generates second complex data by orthogonally detecting the same data as the received data using a second cutoff frequency and a second center frequency lower than the first center frequency; a B-mode processing unit that generates a B-mode image using amplitude information of at least one of the first complex data or the second complex data; a phase (Continued)

difference calculation unit that calculates a first phase difference between frames using phase information of the first complex data and calculates a second phase difference between frames using phase information of the second complex data; a phase difference correction unit that corrects the first phase difference using the second phase difference; and a displacement amount calculation unit that calculates an amount of displacement of a measurement target tissue of the subject using the corrected first phase difference.

19 Claims, 11 Drawing Sheets

(51) Int. Cl.
*G01S 7/52* (2006.01)
*A61B 8/14* (2006.01)
*A61B 8/00* (2006.01)

(52) U.S. Cl.
CPC ...... *G01S 7/52026* (2013.01); *G01S 7/52042* (2013.01); *G01S 7/52077* (2013.01); *G01S 15/8915* (2013.01); *G01S 15/8986* (2013.01); *A61B 8/08* (2013.01); *G01S 7/52039* (2013.01)

(58) Field of Classification Search
CPC ............ G01S 7/52026; G01S 7/52077; G01S 7/52042; G01S 15/8915; G01S 7/52039
See application file for complete search history.

(56) References Cited

FOREIGN PATENT DOCUMENTS

| JP | 10005226 A | * | 1/1998 | ............... A61B 8/00 |
| JP | 2003-325520 A | | 11/2003 | |
| JP | 2003325520 A | * | 11/2003 | ............... A61B 8/08 |
| JP | 4113377 B2 | | 7/2008 | |
| WO | WO 2006/025364 A1 | | 3/2006 | |

OTHER PUBLICATIONS

European Office Action, dated Jul. 16, 2020, for corresponding European Application No. 16861978.1.
European Office Communication for corresponding European Application No. 16861978.1, dated Dec. 3, 2019.
International Preliminary Report on Patentability and Written Opinion of the International Searching Authority (forms PCT/IB/373, PCT/ISA/237 and PCT/IB/326), dated May 17, 2018, for corresponding International Application No. PCT/JP2016/081733, with an English translation of the Written Opinion.
International Search Report (form PCT/ISA/210), dated Jan. 17, 2017, for corresponding International Application No. PCT/JP2016/081733, with an English translation.
Chang et al., "A Novel Envelope Detector for High-Frame Rate, High-Frequency Ultrasound Imaging", IEEE Transactions on Ultrasonics, Ferroelectronics and Frequency Control, vol. 54, No. 9, Sep. 1, 2007, pp. 1792-1801, XP055428994.
Extended European Search Report dated Oct. 29, 2018 for Application No. 16861978.1.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2016/081733 filed on Oct. 26, 2016, which claims priority under 35 U.S.C. § 119(a) to Japanese Patent Application No. 2015-215611 filed on Nov. 2, 2015. The above application is hereby expressly incorporated by reference, in its entirety, into the present application.

BACKGROUND OF THE INVENTION

1. Field of the Invention

The present invention relates to an ultrasound diagnostic apparatus and a control method of an ultrasound diagnostic apparatus, and in particular, to a.

2. Description of the Related Art

Conventionally, in the medical field, an ultrasound diagnostic apparatus using an ultrasound image has been put into practical use. In general, this type of ultrasound diagnostic apparatus generates a B (brightness)-mode image by transmitting an ultrasound beam toward a subject from an ultrasound probe including an array transducer built thereinto, receiving an ultrasound echo from the subject using the ultrasound probe, and electrically processing the received signal.

In order to track the movement of the measurement target tissue, such as a vascular wall, the amount of displacement of the measurement target tissue between frames is calculated.

In such a calculation, transmission of ultrasound pulses from the ultrasound probe to the subject and reception of ultrasound echoes from the subject are repeatedly performed. Every time an ultrasound wave is transmitted or received, the received data is phased and added and orthogonally detected, thereby obtaining complex data including phase information. A phase difference between frames is obtained from the phase information of the obtained complex data. By calculating the amount of displacement from the phase difference, it is possible to track the movement of the measurement target tissue between frames.

However, the maximum speed of the movement of the measurement target tissue that can be tracked is limited according to the repetition frequency. Accordingly, in a case where the measurement target tissue moves at a speed exceeding the maximum speed, aliasing occurs. This may cause an error in the tracking result. In order to prevent such aliasing, it is conceivable to increase the frame rate. However, in a case where the frame rate is increased, there is a problem that the observation region narrows or the image quality of the B-mode image is lowered.

Therefore, JP4113377B discloses an ultrasound diagnostic apparatus that transmits low-frequency ultrasound pulses and high-frequency ultrasound pulses from an ultrasound probe to a subject and prevents aliasing of a phase difference between frames obtained by the high-frequency ultrasound pulses using a phase difference between frames obtained by low-frequency ultrasound pulses.

SUMMARY OF THE INVENTION

However, in the case of transmitting low-frequency ultrasound pulses and high-frequency ultrasound pulses as in the ultrasound diagnostic apparatus disclosed in JP4113377B, the frame rate may be halved.

The present invention has been made in order to solve such a conventional problem, and it is an object of the present invention to provide an ultrasound diagnostic apparatus and a control method of an ultrasound diagnostic apparatus capable of accurately calculating the amount of displacement of a measurement target tissue while maintaining the frame rate.

An ultrasound diagnostic apparatus according to the present invention comprises: an ultrasound probe; a transmission and reception unit that transmits an ultrasound beam from the ultrasound probe toward a subject, receives an ultrasound beam reflected from the subject, and processes a received signal output from the ultrasound probe to generate received data; a complex data generation unit that generates first complex data including amplitude information and phase information by orthogonally detecting the received data generated by the transmission and reception unit using a first center frequency and a first cutoff frequency and generates second complex data by orthogonally detecting the same data as the received data using a second cutoff frequency and a second center frequency lower than the first center frequency; a B-mode processing unit that generates a B-mode image using amplitude information of at least one of the first complex data or the second complex data; a phase difference calculation unit that calculates a first phase difference between frames using phase information of the first complex data and calculates a second phase difference between frames using phase information of the second complex data; a phase difference correction unit that corrects the first phase difference using the second phase difference; and a displacement amount calculation unit that calculates an amount of displacement of a measurement target tissue of the subject using the corrected first phase difference.

It is preferable that the first cutoff frequency is higher than the second cutoff frequency, and it is preferable to further comprise a number-of-times-of-aliasing determination unit that determines the number of times of aliasing of the first phase difference based on the second phase difference.

The number-of-times-of-aliasing determination unit may be configured to be able to calculate at least one candidate for the number of times of aliasing based on the first center frequency, the second center frequency, the first cutoff frequency, and the second cutoff frequency, and determine the number of times of aliasing of the first phase difference from the at least one candidate for the number of times of aliasing.

The number-of-times-of-aliasing determination unit can determine whether the second phase difference is positive or negative, and set an integer part of $C1/C2$ as a maximum value of a candidate for the number of times of aliasing assuming that the first center frequency is $C1$ and the second center frequency is $C2$. In a case where the second phase difference is positive, the number-of-times-of-aliasing determination unit can calculate at least one candidate for the number of times of aliasing satisfying $\pi \times (C2/C1) \times (2n+1) + W1 > \theta 2 \geq \pi \times (C2/C1) \times (2n-1) - W2$ assuming that the second phase difference is $\theta 2$, the candidate for the number of times of aliasing is $n$, and adjustment values each of which is any value are $W1$ and $W2$. In a case where the second phase difference is negative, the number-of-times-of-aliasing determination unit can calculate at least one candidate for the number of times of aliasing satisfying $\pi \times (C2/C1) \times (2n+1) - W1 \leq \theta 2 < \pi \times (C2/C1) \times (2n-1) + W2$. In a case where a plurality of candidates for the number of times of aliasing are calculated, the number-of-times-of-aliasing determination unit can determine n at which a value of an evaluation function $\Delta e(n)=|\theta 1+2\pi n-(C1/C2)\times\theta 2|$ is minimized, assuming that the first phase difference is $\theta 1$, as the number of times of aliasing N of the first phase difference.

The phase difference correction unit may be configured to correct the first phase difference using the second phase difference calculated from only phase information of the second complex data at a representative point of the measurement target tissue of the subject.

The transmission and reception unit can be configured to transmit and receive an ultrasound beam according to a pulse inversion method using a first pulse signal and a second pulse signal of which phases are inverted from each other, and the complex data generation unit can be configured to generate the first complex data from a sum signal of received data corresponding to the first pulse signal and received data corresponding to the second pulse signal and generate the second complex data from a difference signal between received data corresponding to the first pulse signal and received data corresponding to the second pulse signal.

The ultrasound diagnostic apparatus according to the present invention may be configured to further comprise: a quadrature detection condition memory in which a plurality of quadrature detection conditions including a first center frequency condition, a second center frequency condition, a first cutoff frequency condition, and a second cutoff frequency condition, which are set for each of a plurality of the ultrasound probes, are stored in advance; and a device control unit that selects the quadrature detection condition corresponding to the ultrasound probe from the plurality of quadrature detection conditions stored in the quadrature detection condition memory and controls the complex data generation unit to generate complex data based on the quadrature detection condition.

The ultrasound diagnostic apparatus according to the present invention may be configured to further comprise an elasticity index calculation unit that calculates an elasticity index of the measurement target tissue using the amount of displacement of the measurement target tissue of the subject.

A control method of an ultrasound diagnostic apparatus according to the present invention comprises: a step of transmitting an ultrasound beam from a ultrasound probe toward a subject, receiving an ultrasound beam reflected from the subject, and processing a received signal output from the ultrasound probe to generate received data; a step of generating first complex data including amplitude information and phase information by orthogonally detecting the received data using a first center frequency and a first cutoff frequency and generating second complex data by orthogonally detecting the same data as the received data using a second cutoff frequency and a second center frequency lower than the first center frequency; a step of generating a B-mode image using amplitude information of at least one of the first complex data or the second complex data; a step of calculating a first phase difference between frames using phase information of the first complex data and calculating a second phase difference between frames using phase information of the second complex data; a step of correcting the first phase difference using the second phase difference; and a step of calculating an amount of displacement of a measurement target tissue of the subject using the corrected first phase difference.

According to the present invention, the first complex data including the amplitude information and the phase information is generated by orthogonally detecting the received data using the first center frequency and the first cutoff frequency and the second complex data is generated by orthogonally detecting the same data as the received data using the second cutoff frequency and the second center frequency lower than the first center frequency, the first phase difference between frames is calculated using the phase information of the first complex data and the second phase difference between frames is calculated using the phase information of the second complex data, the first phase difference is corrected using the second phase difference, and the amount of displacement of the measurement target tissue of the subject is calculated using the corrected first phase difference. Therefore, it is possible to amount of displacement of the measurement target tissue.

DESCRIPTION OF THE PREFERRED EMBODIMENTS

Hereinafter, embodiments of the present invention will be described with reference to the accompanying diagrams.

First Embodiment

Figure 1:
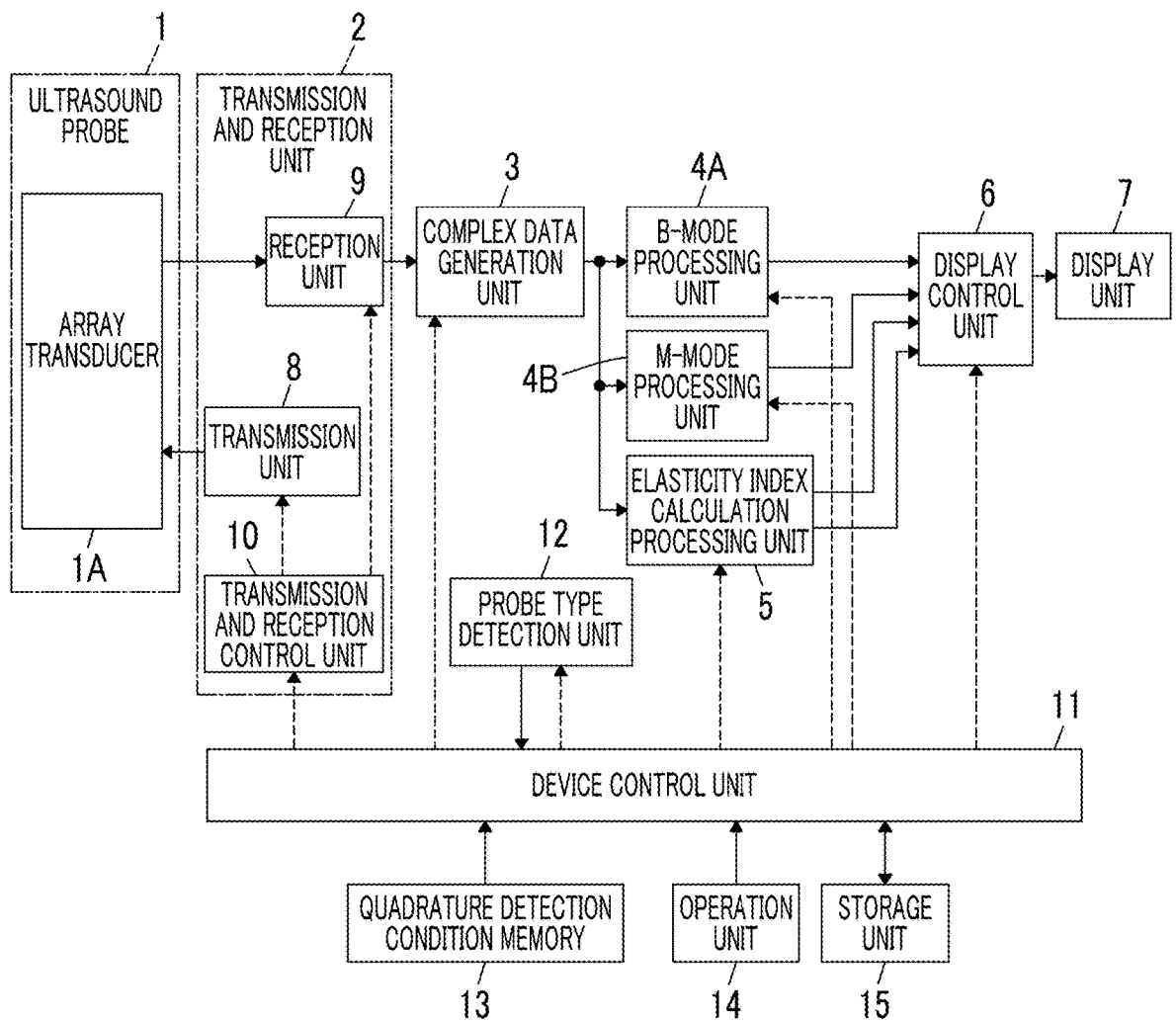
FIG. 1 is a block diagram showing the configuration of an ultrasound diagnostic apparatus according to a first embodiment of the present invention.

FIG. 1 shows the configuration of an ultrasound diagnostic apparatus according to a first embodiment of the present invention. The ultrasound diagnostic apparatus includes an ultrasound probe 1 including a transducer array 1A built thereinto, and a complex data generation unit 3 is connected to the ultrasound probe 1 through a transmission and reception unit 2. A B-mode processing unit 4A, an M (motion)-mode processing unit 4B, and an elasticity index calculation processing unit 5 are connected in parallel to the complex data generation unit 3, and a display unit 7 is connected to the B-mode processing unit 4A, the M-mode processing unit 4B, and the elasticity index calculation processing unit 5 through a display control unit 6.

The transmission and reception unit 2 has a transmission unit 8 and a reception unit 9, which are connected to the transducer array 1A of the ultrasound probe 1, and a transmission and reception control unit 10 connected to the transmission unit 8 and the reception unit 9.

A device control unit 11 is connected to the transmission and reception control unit 10 of the transmission and reception unit 2, the complex data generation unit 3, the B-mode processing unit 4A, the M-mode processing unit 4B, the elasticity index calculation processing unit 5, and the display control unit 6. In addition, a probe type detection unit 12, a quadrature detection condition memory 13, an operation unit 14, and a storage unit 15 are connected to the device control unit 11.

The transducer array 1A of the ultrasound probe 1 has a plurality of ultrasound transducers arranged in a one-dimensional or two-dimensional manner. Each of the ultrasound transducers transmits an ultrasound wave according to a driving signal supplied from the transmission unit 8, receives an ultrasound echo from the subject, and outputs the received signal. For example, each ultrasound transducer is formed by a transducer in which electrodes are formed at both ends of the piezoelectric body formed of piezoelectric ceramic represented by lead zirconate titanate (PZT), a polymer piezoelectric element represented by polyvinylidene fluoride (PVDF), piezoelectric single crystal represented by lead magnesium niobate-lead titanate (PMN-PT), or the like.

In a case where a pulsed or continuous-wave voltage is applied to the electrodes of such a transducer, the piezoelectric body expands and contracts to generate pulsed or continuous-wave ultrasound waves from each transducer. By combining these ultrasound waves, an ultrasound beam is formed. In addition, the respective transducers expand and contract by receiving the propagating ultrasound waves, thereby generating electrical signals. These electrical signals are output as received signals of the ultrasound waves.

The transmission and reception unit 2 transmits and receives an ultrasound beam. The transmission unit 8 of the transmission and reception unit 2 includes, for example, a plurality of pulse generators. Based on a transmission delay pattern selected according to the control signal from the transmission and reception control unit 10, the transmission unit 8 of the transmission and reception unit 2 adjusts the amount of delay of each driving signal so that ultrasound waves transmitted from the plurality of ultrasound transducers of the transducer array 1A form an ultrasound beam, and supplies the adjusted signals to the plurality of ultrasound transducers.

Figure 2:
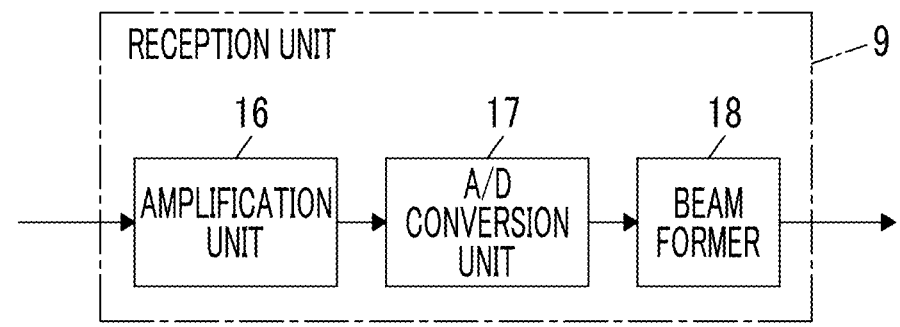
FIG. 2 is a block diagram showing the internal configuration of a reception unit.

As shown in FIG. 2, the reception unit 9 of the transmission and reception unit 2 has a configuration in which an amplification unit 16, an analog/digital (A/D) conversion unit 17, and a beam former 18 are sequentially connected in series. In the reception unit 9, the amplification unit 16 amplifies a received signal transmitted from each ultrasound transducer of the transducer array 1A, the A/D conversion unit 17 performs A/D conversion of the received signal, and then the beam former 18 adds the received data with a delay according to the sound speed set based on a reception delay pattern selected according to the control signal from the transmission and reception control unit 10 or the distribution of the sound speed, thereby performing reception focus processing. Through the reception focusing processing, a sound ray signal with a narrowed focus of ultrasound echo due to is generated.

Based on various control signals transmitted from the device control unit 11, the transmission and reception control unit 10 controls the transmission unit 8 and the reception unit 9 so that transmission of ultrasound pulses to the subject and reception of ultrasound echoes from the subject are repeatedly performed.

Figure 3:
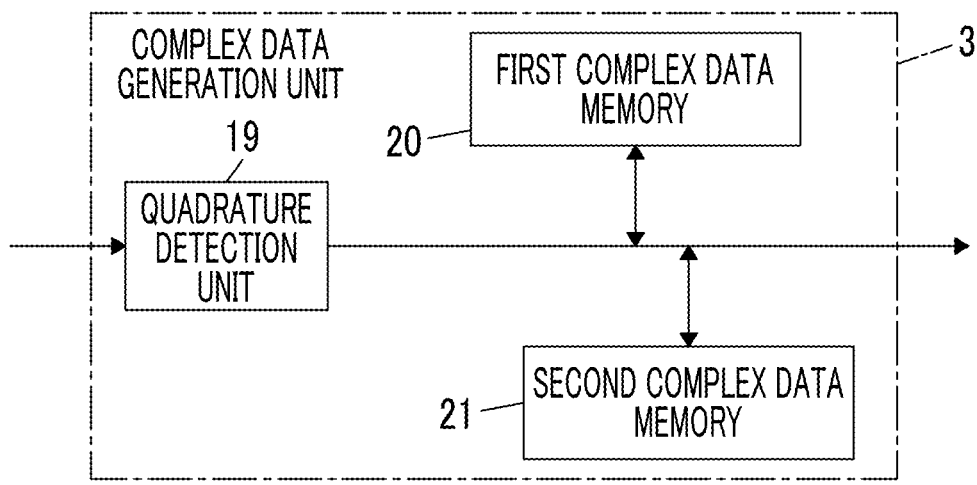
FIG. 3 is a block diagram showing the internal configuration of a complex data generation unit.

The complex data generation unit 3 generates complex data including amplitude information and phase information by quadrature detection. As shown in FIG. 3, the complex data generation unit has a configuration in which a first complex data memory 20 and a second complex data memory 21 are connected in parallel to the output terminal of a quadrature detection unit 19.

The quadrature detection unit 19 generates first complex data by mixing a carrier signal having a first center frequency with the received data generated by the transmission and reception unit 2 and performing filtering using a first cutoff frequency. In addition, the quadrature detection unit 19 generates second complex data by mixing a carrier signal having a second center frequency, which is lower than the first center frequency, with the same data as the received data generated by the transmission and reception unit 2 and performing filtering using a second cutoff frequency lower than the first cutoff frequency.

The first complex data memory 20 sequentially stores the first complex data generated by the quadrature detection unit 19 for each frame, and the second complex data memory 21 sequentially stores the second complex data generated by the quadrature detection unit 19 for each frame.

Figure 4A:
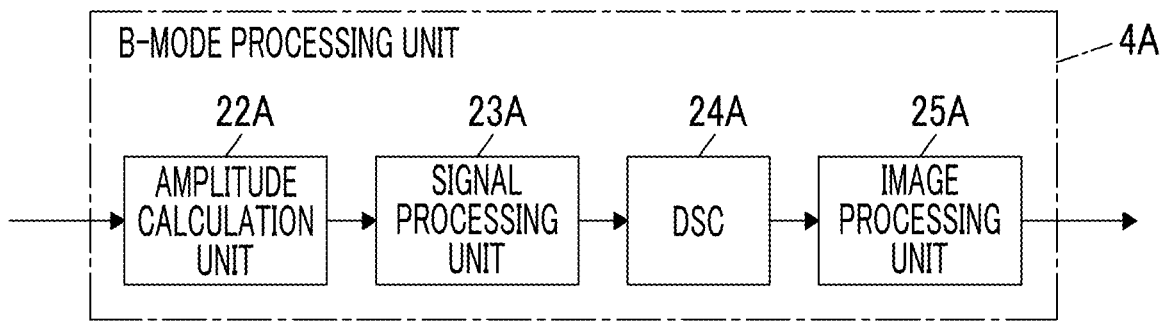
FIG. 4A is a block diagram showing the internal configuration of a B-mode processing unit.

As shown in FIG. 4A, the B-mode processing unit 4A has a configuration in which an amplitude calculation unit 22A, a signal processing unit 23A, a digital scan converter (DSC) 24A, and an image processing unit 25A are sequentially connected in series.

The amplitude calculation unit 22A extracts amplitude information from the first complex data and the second complex data generated by the complex data generation unit 3, and the signal processing unit 23A corrects the attenuation by the distance according to the depth of the reflection position of the ultrasound wave by using the amplitude information of both the first complex data and the second complex data extracted by the amplitude calculation unit 22A and then performs envelope detection processing and further performs various kinds of required image processing, such as gradation processing. As a result, a B-mode image signal that is tomographic image information regarding tissues in the subject is generated.

The DSC 24A converts the B-mode image signal generated by the signal processing unit 23A into an image signal according to the normal television signal scanning method (raster conversion).

The image processing unit 25A performs various kinds of required image processing, such as gradation processing, on the B-mode image signal input from the DSC 24A, and then outputs the B-mode image signal to the display control unit 6.

The B-mode processing unit 4A can perform B-mode processing even in a case where only one of the amplitude information included in the first complex data and the amplitude information included in the second complex data is used.

Figure 4B:
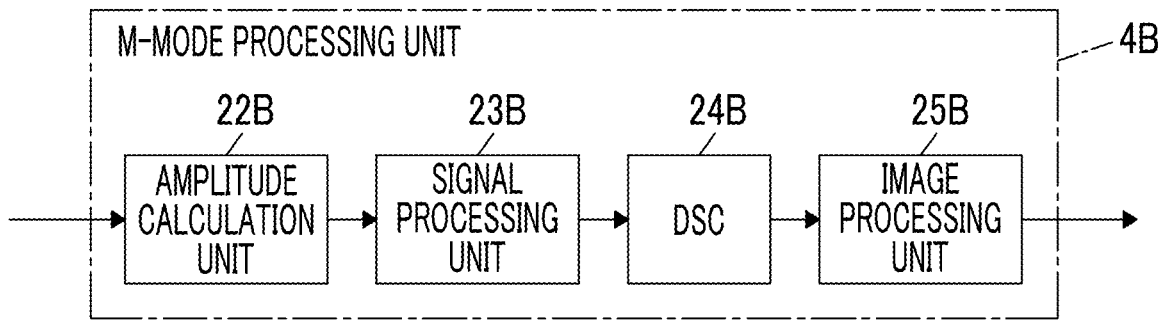
FIG. 4B is a block diagram showing the internal configuration of an M-mode processing unit.
Figure 5:
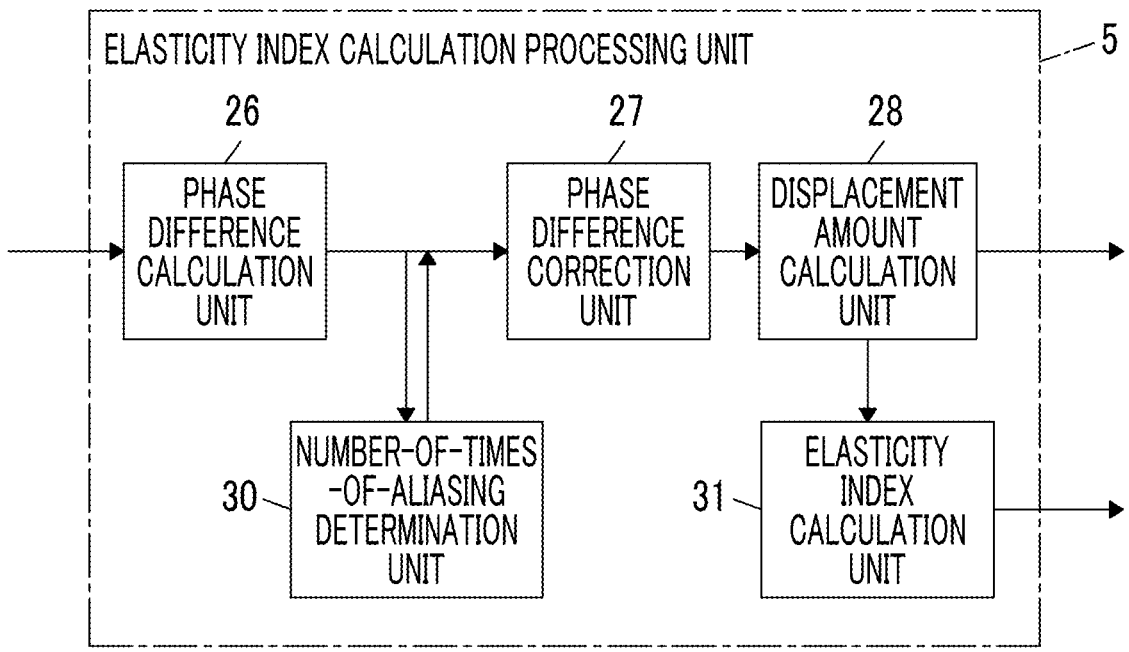
FIG. 5 is a block diagram showing the internal configuration of an elasticity index calculation processing unit.

As shown in FIG. 4B, the M-mode processing unit 4B has a configuration in which an amplitude calculation unit 22B, a signal processing unit 23B, a DSC 24B, and an image processing unit 25B are sequentially connected in series.

The amplitude calculation unit 22B extracts amplitude information from the first complex data and the second complex data generated by the complex data generation unit 3, and the signal processing unit 23B corrects the attenuation by the distance according to the depth of the reflection position of the ultrasound wave by using the amplitude information of both the first complex data and the second complex data extracted by the amplitude calculation unit 22B and then performs envelope detection processing and further performs various kinds of required image processing, such as gradation processing, thereby generating tomographic image information regarding tissues in the subject. The DSC 24B converts the tomographic image information on the designated one scan line into an image signal so as to be aligned on the time axis. As a result, an M-mode image signal is generated. The M-mode image is a tomographic image of a measurement target tissue with the horizontal axis as a time axis and the vertical axis as a brightness axis, and the tomographic image changes in the direction of the vertical axis according to the amount of displacement of the measurement target tissue.

The image processing unit 25B performs various kinds of required image processing, such as gradation processing, on the M-mode image signal input from the DSC 24B, and then outputs the M-mode image signal to the display control unit 6.

The M-mode processing unit 4B can perform M-mode processing even in a case where only one of the amplitude information included in the first complex data and the amplitude information included in the second complex data is used.

The elasticity index calculation processing unit 5 has a configuration in which a phase difference calculation unit 26, a phase difference correction unit 27, and a displacement amount calculation unit 28 are sequentially connected in series, a number-of-times-of-aliasing determination unit 30 is connected to the output terminal of the phase difference calculation unit 26, and an elasticity index calculation unit 31 is connected to the displacement amount calculation unit 28.

The phase difference calculation unit 26 calculates a first phase difference between frames by comparing pieces of phase information included in the first complex data sequentially stored for each frame in the first complex data memory 20. The phase difference calculation unit 26 calculates a second phase difference between frames by comparing pieces of phase information included in the second complex data sequentially stored for each frame in the second complex data memory 21.

The number-of-times-of-aliasing determination unit 30 determines the number of times of aliasing occurring at the first phase difference based on the second phase difference calculated by the phase difference calculation unit 26.

The phase difference correction unit 27 corrects the first phase difference based on the number of times of aliasing of the first phase difference determined by the number-of-times-of-aliasing determination unit 30 and the second phase difference calculated by the phase difference calculation unit 26.

The displacement amount calculation unit 28 calculates the amount of displacement between frames of the measurement target tissue of the subject, such as a vascular wall, using the first phase difference corrected by the phase difference correction unit 27, and outputs the calculated amount of displacement to the elasticity index calculation unit 31 and the display unit 7.

The elasticity index calculation unit 31 calculates an elasticity index, such as the modulus of elasticity, the strain, the stiffness parameter, and the diameter change amount of the measurement target tissue, using the amount of displacement of the measurement target tissue calculated by the displacement amount calculation unit 28, and outputs the calculated elasticity index to the display unit 7.

The display control unit 6 displays the B-mode image on the display unit 7 based on the B-mode image signal generated by the B-mode processing unit 4A, and displays the M-mode image on the display unit 7 based on the M-mode image signal generated by the M-mode processing unit 4B. The movement of the measurement target tissue that changes according to the amount of displacement calculated by the displacement amount calculation unit 28 may be displayed on the M-mode image, or the elasticity index calculated by the elasticity index calculation unit 31 may be displayed on the display unit 7.

The display unit 7 includes, for example, a display device, such as a liquid crystal display (LCD), and displays the B-mode image and the M-mode image under the control of the display control unit 6.

The probe type detection unit 12 detects the type of the ultrasound probe 1 connected to the transmission and reception unit 2, and outputs information on the detected type of the ultrasound probe 1 to the device control unit 11.

The quadrature detection condition memory 13 stores a plurality of quadrature detection conditions, which are set for a plurality of ultrasound probes, in advance. The plurality of quadrature detection conditions are for performing quadrature detection suitable for the frequency band of the detected ultrasound probe.

The device control unit 11 controls the transmission and reception control unit 10, the complex data generation unit 3, the B-mode processing unit 4A, the M-mode processing unit 4B, the elasticity index calculation processing unit 5, the display control unit 6, and the probe type detection unit 12 based on an instruction input by the operator through the operation unit 14.

The operation unit 14 is used in a case where the operator performs an input operation, and can be formed by a keyboard, a mouse, a trackball, a touch panel, and the like.

The storage unit 15 stores an operation program and the like, and recording media, such as a hard disk, a flexible disk, an MO, an MT, a RAM, a CD-ROM, a DVD-ROM, an SD card, a CF card, and a USB memory, or a server may be used.

Here, the operation of the quadrature detection unit 19 of the complex data generation unit 3 will be described.

Figure 6:
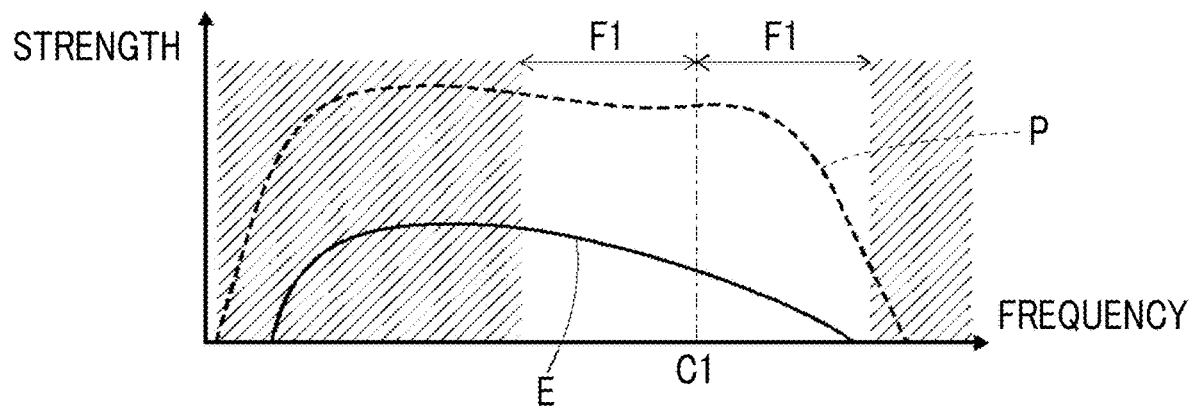
FIG. 6 is a graph showing a first center frequency and a first cutoff frequency.

FIG. 6 is a graph showing a frequency band P of the ultrasound probe 1 and a frequency band E of ultrasound echoes from the subject. In FIG. 6, the horizontal axis indicates the frequency of the ultrasound wave, and the vertical axis indicates the strength of the ultrasound wave. The ultrasound probe 1 transmits ultrasound waves within the range of the frequency band P, and receives ultrasound echoes within the range of the frequency band E.

Under the control of the device control unit 11, the quadrature detection unit 19 orthogonally detects the received data using a first center frequency C1 and a first cutoff frequency F1 to generate first complex data. In this case, a filter having a bandwidth from a value obtained by adding the first cutoff frequency F1 to the first center frequency C1 to a value obtained by subtracting the first cutoff frequency F1 from the first center frequency C1 is set.

Figure 7:
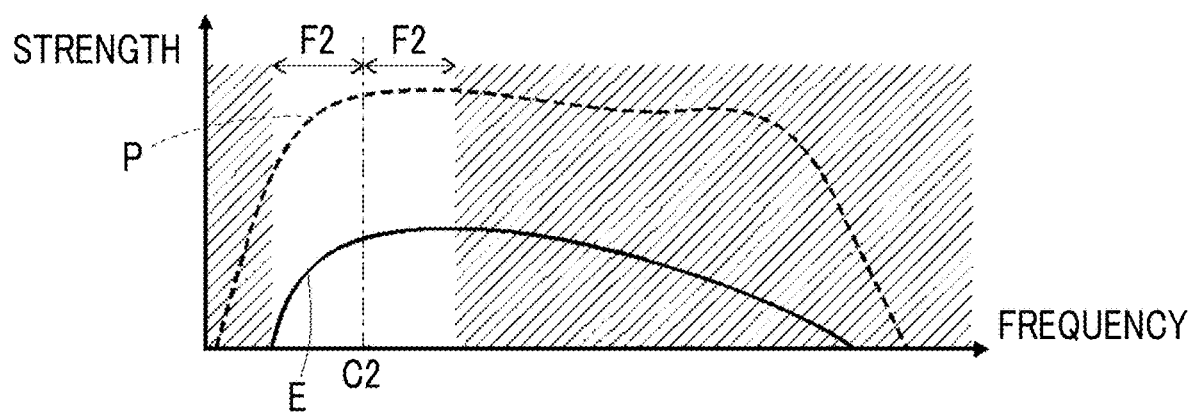
FIG. 7 is a graph showing a second center frequency and a second cutoff frequency.

The quadrature detection unit 19 orthogonally detects the same received data as the received data, which is orthogonally detected using the first center frequency C1 and the first cutoff frequency F1, using a second center frequency C2 and a second cutoff frequency F2 to generate second complex data. In this case, as shown in FIG. 7, a filter having a bandwidth from a value obtained by adding the second cutoff frequency F2 to the second center frequency C2 to a value obtained by subtracting the second cutoff frequency F2 from the second center frequency C2 is set.

Here, as the first center frequency C1 and the first cutoff frequency F1, the first center frequency C1 and the small first cutoff frequency F1 in a high frequency region are set so that the amount of displacement can be obtained with high resolution and high accuracy. As the second center frequency C2 and the second cutoff frequency F2, the second center frequency C2 lower than the first center frequency C1 and the second cutoff frequency F2 smaller than the first cutoff frequency F1 are set so that the signal noise (SN) ratio is high and the robustness against aliasing noise is high.

Figure 8A:
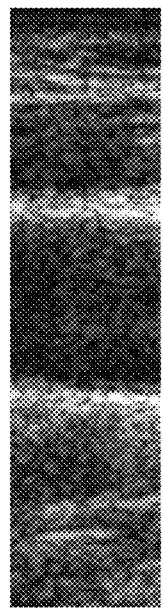
FIG. 8A is a diagram showing an example of a B-mode image in which the center frequency is set to 10 MHz.
Figure 8B:
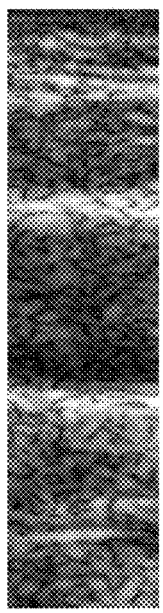
FIG. 8B is a diagram showing an example of a B-mode image in which the center frequency is set to 6 MHz.

FIG. 8A is a B-mode image of the carotid artery created by setting the frame rate to 50 frames/second and the center frequency to 10 MHz, and FIG. 8B is a B-mode image of the carotid artery created by setting the frame rate to 50 frames/second and the center frequency to 6 MHz. The B-mode image in FIG. 8A in which the center frequency is set in a relatively high frequency region has higher resolution than the B-mode image in FIG. 8B.

Figure 9A:
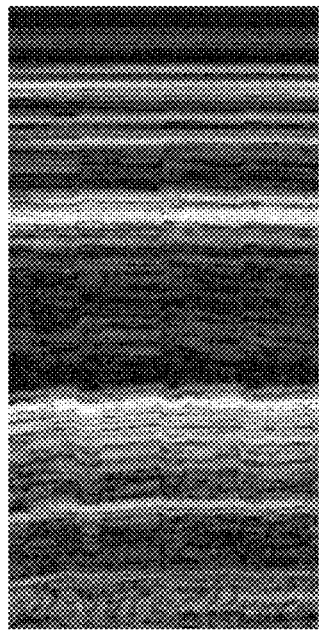
FIG. 9A is a diagram showing an example of an M-mode image in which the center frequency is set to 10 MHz.
Figure 9B:
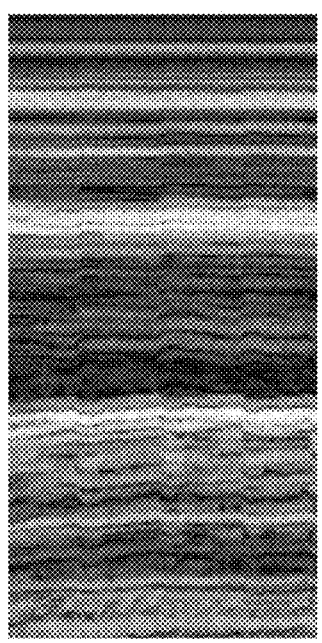
FIG. 9B is a diagram showing an example of an M-mode image in which the center frequency is set to 6 MHz.

FIG. 9A is an M-mode image of the carotid artery created by setting the frame rate to 50 frames/second and the center frequency to 10 MHz, and FIG. 9B is an M-mode image of the carotid artery created by setting the frame rate to 50 frames/second and the center frequency to 6 MHz. The M-mode image in FIG. 9A in which the center frequency is set in a relatively high frequency region has higher resolution than the M-mode image in FIG. 9B.

Figure 10A:
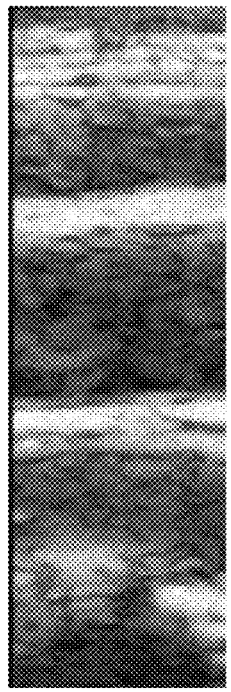
FIG. 10A is a diagram showing an example of a B-mode image in which the cutoff frequency is set to 1.5 MHz.
Figure 10B:
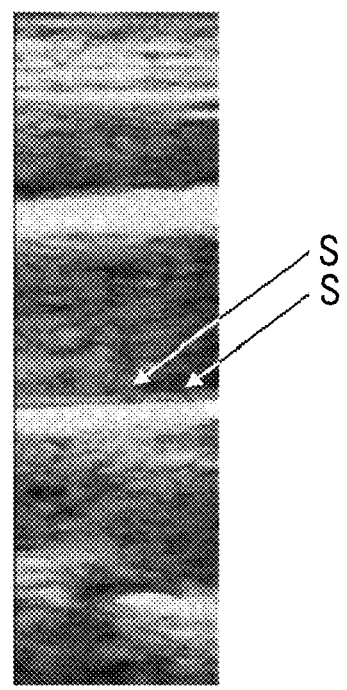
FIG. 10B is a diagram showing an example of a B-mode image in which the cutoff frequency is set to 3.5 MHz.

FIG. 10A is a B-mode image of the carotid artery created by setting the frame rate to 50 frames/second, the center frequency to 6 MHz, and the cutoff frequency to 1.5 MHz, and FIG. 10B is a B-mode image of the carotid artery created by setting the frame rate to 50 frames/second, the center frequency to 6 MHz, and the cutoff frequency to 3.5 MHz. Comparing FIG. 10A with FIG. 10B, in the B-mode image shown in FIG. 10B, a break S is generated between the intravascular lumen and the intima boundary. This is because the cutoff frequency is relatively high and accordingly the bandwidth of the filter expands and the SN ratio decreases and accordingly the influence of noise in a low frequency region is received. On the other hand, in the B-mode image shown in FIG. 10A in which a relatively small cutoff frequency is set, the SN ratio is high. Therefore, the break S shown in FIG. 10B is not generated.

The phase difference calculation unit 26 of the elasticity index calculation processing unit 5 calculates a first phase difference and a second phase difference between frames using the phase information included in the first complex data and the second complex data generated by the complex data generation unit 3.

Complex data Z is expressed as Z=I+jQ, where t is time, d is sampling depth, real part is I(t, d), and imaginary part is Q(t, d). Assuming that the phase difference between frames is $\Delta\theta$, $\Delta\theta$ can be calculated by the following Equation (1) using the complex data Z for each region of interest (ROI) in the depth direction with $\Delta T$ as an inter-frame time, that is, 1/frame rate, and D as a distance interval in the depth direction between sampling points of complex data.

$$e^{j\Delta\theta(t+\frac{\Delta T}{2})} = \frac{\sum_{m:ROI} z(t+\Delta T; d+mD) \cdot z^*(t; d+mD)}{\left|\sum_{m:ROI} z(t+\Delta T; d+mD) \cdot z^*(t; d+mD)\right|} \quad (1)$$

With respect to the first phase difference calculated as described above by the phase difference calculation unit 26, based on the second phase difference, the number-of-times-of-aliasing determination unit 30 of the elasticity index calculation processing unit 5 determines the number of times of aliasing of the first phase difference.

The number-of-times-of-aliasing determination unit 30 calculates a candidate for the number of times of aliasing of the first phase difference, and determines the number of times of aliasing from a plurality of candidates for the number of times of aliasing in a case where the candidates for the number of times of aliasing are calculated.

First, the number-of-times-of-aliasing determination unit 30 calculates candidates for the number of times of aliasing with the first center frequency as C1, the second center frequency as C2, and the integer part of the ratio C1/C2 as a maximum value of the number of times of aliasing. Specifically, all integers whose absolute values are equal to or less than the integer part of the ratio C1/C2 are candidates for the number of times of aliasing. For example, in a case where the integer part of the ratio C1/C2 is 2, candidates for the number of times of aliasing are 0, 1, 2, −1, and −2.

Then, it is determined whether the second phase difference is positive or negative. In a case where the second phase difference is positive, a candidate n for the number of times of aliasing is calculated so as to satisfy the following Expression (2) with the second phase difference as $\theta 2$, the candidate for the number of times of aliasing as n, and the adjustment values of a threshold value considering noise and the like as W1 and W2.

$$\pi \times (C2/C1) \times (2n+1) + W1 > \theta 2 \geq \pi \times (C2/C1) \times (2n-1) - W2 \quad (2)$$

The adjustment values W1 and W2 can be set to values of about $\pi/4$. Then, using the adjustment values W1 and W2, a boundary region where the phase differences overlap each other is set in a phase difference section in which the number of times of aliasing changes.

Each candidate for the number of times of aliasing is substituted into Expression (2). In a case where there is only one candidate for the number of times of aliasing that satisfies Expression (2), the candidate n for the number of times of aliasing is determined as the number of times of aliasing N of the first phase difference. On the other hand, in a case where a plurality of candidates for the number of times of aliasing satisfy Expression (2), each of the plurality of candidates n for the number of times of aliasing is substituted into the following Equation (3) with the first phase difference as $\theta 1$, and the candidate n for the number of times of aliasing at which the value of the evaluation function is minimized is determined as the number of times of aliasing N of the first phase difference.

$$\text{Evaluation function } \Delta e(n) = |\theta 1 + 2\pi n - (C1/C2) \times \theta 2| \quad (3)$$

Here, $(C1/C2) \times \theta 2$ in Equation (3) indicates a provisional first phase difference estimated in a case where it is assumed that the ratio between the first center frequency C1 and the second center frequency C2 is approximately equal to the ratio between the first phase difference θ1 and the second phase difference θ2. Each of the plurality of candidates n for the number of times of aliasing is substituted into the evaluation function of Equation (3), values of the evaluation function are compared, and the candidate n for the number of times of aliasing at which the first phase difference θ1 after the addition of 2πn is closest to the provisional first phase difference α and the value of the evaluation function is minimized is determined as the number of times of aliasing N of the first phase difference.

On the other hand, it is determined whether the second phase difference θ2 is positive or negative. In a case where the second phase difference θ2 is negative, the candidate n for the number of times of aliasing is calculated so as to satisfy the following Expression (4).

$$\pi \times (C2/C1) \times (2n+1) - W1 \leq \theta 2 < \pi \times (C2/C1) \times (2n-1) + W2 \quad (4)$$

In this case, each candidate for the number of times of aliasing is substituted into Expression (4). In a case where there is only one candidate for the number of times of aliasing that satisfies Expression (4), the candidate for the number of times of aliasing is determined as the number of times of aliasing N of the first phase difference θ1. On the other hand, in a case where a plurality of candidates n for the number of times of aliasing satisfy Expression (4), each of the plurality of candidates n for the number of times of aliasing is substituted into Equation (3), and the candidate n for the number of times of aliasing at which the value of the evaluation function is minimized is determined as the number of times of aliasing N of the first phase difference.

The phase difference correction unit 27 corrects the first phase difference θ1 based on the second phase difference θ2 and the number of times of aliasing N of the first phase difference θ1 determined by the number-of-times-of-aliasing determination unit 30. Specifically, the phase difference correction unit 27 corrects the first phase difference θ1 so that 2πN is added to the first phase difference θ1 in a case where aliasing occurs N times at the first phase difference θ1 and 2πN is subtracted from the first phase difference θ1 in a case where aliasing occurs -N times at the first phase difference θ1.

Figure 11:
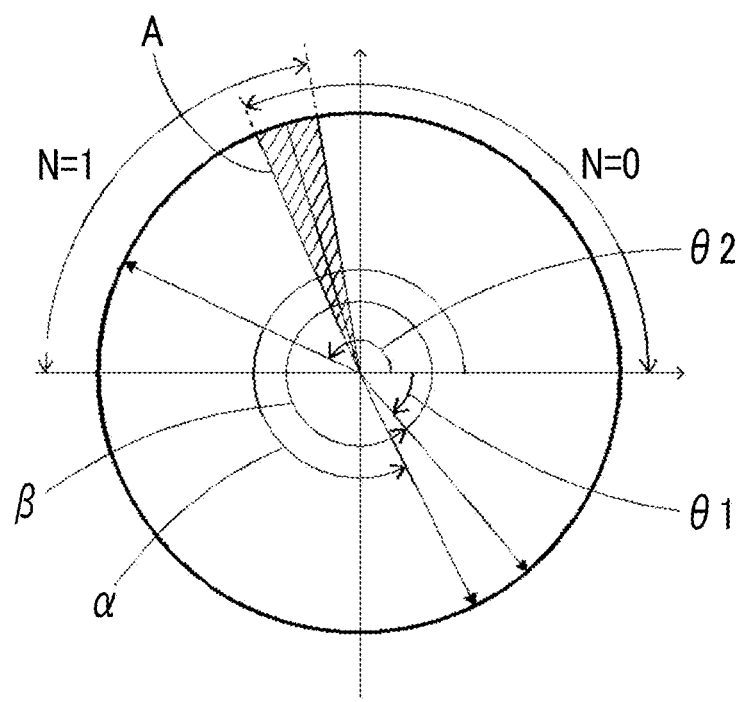
FIG. 11 is a graph showing an example of the correction of a first phase difference.

FIG. 11 shows an example in which the first center frequency C1 is 10 MHz and the second center frequency C2 is 6 MHz, the negative first phase difference θ1 and the positive second phase difference θ2 are calculated by the phase difference calculation unit 26, and the second phase difference θ2 is not located in a boundary region A set in the phase difference section in which the number of times of aliasing changes.

First, since the integer part of the ratio C1/C2 is 1, 0, 1, and -1 that are all candidates for the number of times of aliasing are calculated by the number-of-times-of-aliasing determination unit 30. Then, as shown in FIG. 11, since θ2 is positive, 0 and 1 that are two candidates for the number of times of aliasing satisfying Expression (2) are calculated by substituting each value into Expression (2).

In a case where each of the two candidates for the number of times of aliasing is substituted into Equation (3), the first phase difference θ1 after the addition of 2π×1 and the provisional first phase difference α are closest to each other at the time of n=1, and the value of the evaluation function is minimized. Therefore, the number-of-times-of-aliasing determination unit 30 determines that the number of times N of aliasing occurring at the first phase difference θ1 is one.

As described above, since aliasing occurs once at the first phase difference θ1, the phase difference correction unit 27 performs correction, such as adding a phase β=2π×1 to the first phase difference θ1.

Figure 12:
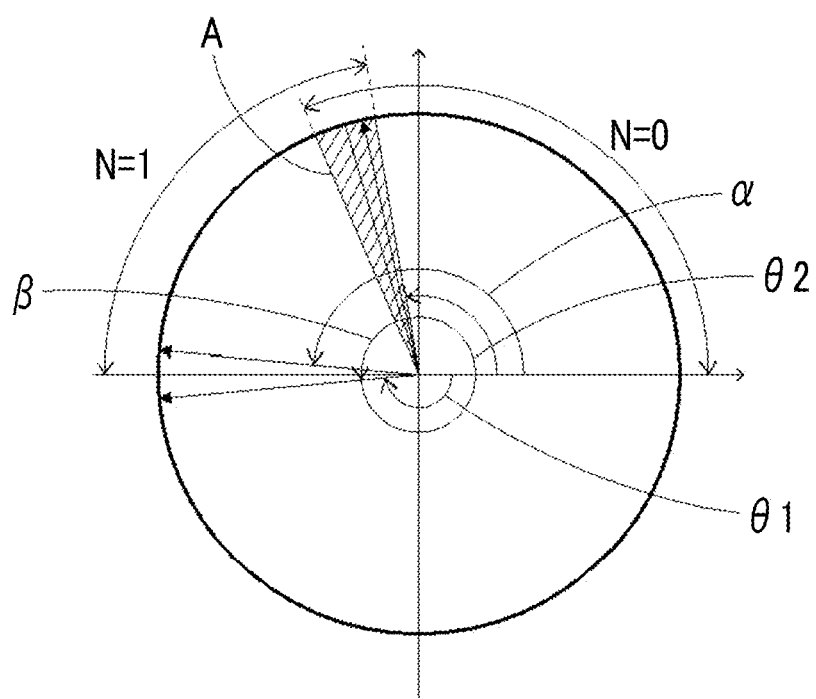
FIG. 12 is a graph showing another example of the correction of a first phase difference.

FIG. 12 shows an example in which the first center frequency C1 is 10 MHz and the second center frequency C2 is 6 MHz, the negative first phase difference θ1 and the positive second phase difference θ2 are calculated by the phase difference calculation unit 26, and the second phase difference θ2 is located in the boundary region A.

First, since the integer part of the ratio C1/C2 is 1, 0, 1, and -1 that are all candidates for the number of times of aliasing are calculated by the number-of-times-of-aliasing determination unit 30. Then, as shown in FIG. 12, since θ2 is positive, 0 and 1 that are two candidates for the number of times of aliasing satisfying Expression (2) are calculated by substituting each value into Expression (2).

In a case where each of the two candidates for the number of times of aliasing is substituted into Equation (3), the first phase difference θ1 after the addition of 2π×1 and the provisional first phase difference α are closest to each other at the time of n=1, and the value of the evaluation function is minimized. Therefore, the number-of-times-of-aliasing determination unit 30 determines that the number of times of aliasing occurring at the first phase difference θ1 is one.

As described above, since aliasing occurs once at the first phase difference θ1, the phase difference correction unit 27 performs correction, such as adding a phase β=2π×1 to the first phase difference θ1.

Figure 13:
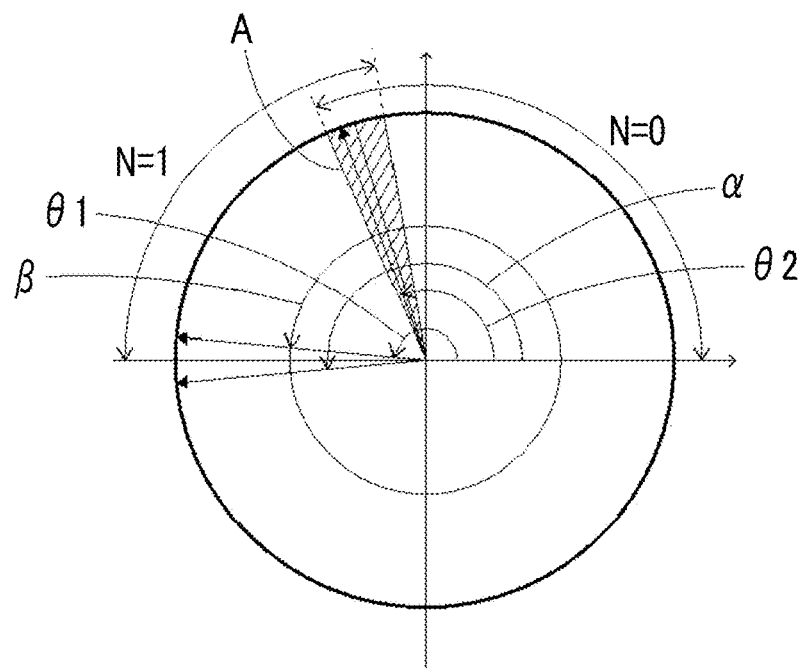
FIG. 13 is a graph showing still another example of the correction of a first phase difference.

FIG. 13 shows an example in which the first center frequency C1 is 10 MHz and the second center frequency C2 is 6 MHz, the positive first phase difference θ1 and the positive second phase difference θ2 are calculated by the phase difference calculation unit 26, and the second phase difference θ2 is located in the boundary region A.

First, since the integer part of the ratio C1/C2 is 1, 0, 1, and -1 that are all candidates for the number of times of aliasing are calculated by the number-of-times-of-aliasing determination unit 30. Then, as shown in FIG. 13, since θ2 is positive, 0 and 1 that are two candidates for the number of times of aliasing satisfying Expression (2) are calculated by substituting each value into Expression (2). In a case where each of the two candidates for the number of times of aliasing is substituted into Equation (3), the first phase difference θ1 after the addition of 2π×0 and the provisional first phase difference α are closest to each other at the time of n=0, and the value of the evaluation function is minimized. Therefore, the number-of-times-of-aliasing determination unit 30 determines that the number of times of aliasing occurring at the first phase difference θ1 is zero, that is, no aliasing occurs. In this case, the phase difference correction unit 27 performs correction, such as adding a phase β=2π×0 to the first phase difference θ1.

In this manner, by considering the boundary region A set by the adjustment values W1 and W2, even in a case where a calculation error occurs due to influence of noise or the like, the number-of-times-of-aliasing determination unit 30 does not erroneously determine the number of times of aliasing of the first phase difference θ1, and the phase difference correction unit 27 can accurately correct the first phase difference θ1.

In addition, as described above, the first phase difference and the second phase difference are extracted from the first complex data and the second complex data, which are calculated by the quadrature detection unit 19, by using the same data as the received data generated by the reception unit 9. For this reason, there is little occurrence of a difference in the presence and absence of noise in received data used in the calculation, and the occurrence of error in correction due to a difference in the presence and absence of noise of received data is also prevented.

By using the first phase difference corrected by the phase difference correction unit 27 as described above, the displacement amount calculation unit 28 of the elasticity index calculation processing unit 5 calculates the amount of displacement of the measurement target tissue.

Assuming that the speed between frames is v, the amount of displacement is $\Delta x$, the sound speed is $C_0$, and the angular speed is $\omega 0 = 2\pi C1$ or $\omega 0 = 2\pi C2$, the speed between frames v and the amount of displacement $\Delta x$ can be calculated by the following Equations (5) and (6).

$$v\left(t + \frac{\Delta T}{2}\right) = -\frac{c_0}{2} \frac{\Delta\theta\left(t + \frac{\Delta T}{2}\right)}{\omega_0 \Delta T} \quad (5)$$

$$\Delta x\left(t + \frac{\Delta T}{2}\right) = v\left(t + \frac{\Delta T}{2}\right) \times \Delta T \quad (6)$$

Then, by adjusting the ROI between frames according to the calculated amount of displacement $\Delta x$ and repeating the calculation of the phase difference, it is possible to track the amount of displacement of the measurement target tissue.

In addition, since the speed v is proportional to the phase difference θ, in a case where aliasing occurs at the phase difference, it is calculated that the measurement target tissue moves in a direction opposite to the actual movement direction. Therefore, since the setting position of the ROI between the next frames is wrong, the tracking of the measurement target tissue fails.

Using the amount of displacement of the measurement target tissue calculated by the displacement amount calculation unit 28 as described above, the elasticity index calculation unit 31 calculates an elasticity index, such as the modulus of elasticity, the strain, the stiffness parameter, and the diameter change amount of the measurement target tissue.

The amount of displacement of the measurement target tissue calculated by the displacement amount calculation unit 28 and the elasticity index of the measurement target tissue calculated by the elasticity index calculation unit 31 measurement target tissue.

Next, the operation of the ultrasound diagnostic apparatus according to the first embodiment will be described.

First, an ultrasound beam is transmitted from a plurality of ultrasound transducers of the transducer array 1A of the ultrasound probe 1 according to a driving signal from the transmission unit 8 of the transmission and reception unit 2, a received signal from each ultrasound transducer that has received the ultrasound echo from the subject is output to the reception unit 9, and the received signal is amplified by the amplification unit 16 of the reception unit 9 and A/D converted by the A/D conversion unit 17. Then, phasing addition is performed by the beam former 18. As a result, received data is generated.

By the quadrature detection unit 19 of the complex data generation unit 3, the received data is orthogonally detected using the first center frequency and the first cutoff frequency and the same data as the received data is orthogonally detected using the second center frequency and the second cutoff frequency. As a result, the first complex data and the second complex data are generated.

In this case, the probe type detection unit 12 detects the type of the ultrasound probe 1, and the device control unit 11 selects an optimal quadrature detection condition, among a plurality of quadrature detection conditions stored in advance in the quadrature detection condition memory 13, based on the type of the ultrasound probe 1 and controls the quadrature detection unit 19. In addition to the type of the ultrasound probe 1, the device control unit 11 can also control the quadrature detection unit 19 based on a mode condition, such as a fundamental wave, a harmonic, and a compound harmonic, and an observation condition (preset) for an observation part.

By operating the operation unit 14 by the operator, it is also possible to adjust the first center frequency, the first cutoff frequency, the second center frequency, and the second cutoff frequency according to the frequency band of the ultrasound probe 1.

The amplitude information of the first complex data and the second complex data generated by the complex data generation unit 3 is extracted by the amplitude calculation unit 22A of the B-mode processing unit 4A, and envelope detection processing is performed on the extracted amplitude information by the signal processing unit 23A to generate a B-mode image signal. The B-mode image signal is output to the display control unit 6 through the DSC 24A and the image processing unit 25A, and a B-mode image is displayed on the display unit 7 by the display control unit 6.

In addition, the amplitude information of the first complex data and the second complex data generated by the complex data generation unit 3 is extracted by the amplitude calculation unit 22B of the M-mode processing unit 4B, and envelope detection processing is performed on the extracted amplitude information by the signal processing unit 23B to generate tomographic image information. By displaying the tomographic image information on one scan line designated by the device control unit 11 so as to be aligned on the time axis by the DSC 24B, an M-mode image signal is obtained. The M-mode image signal is output to the display control unit 6 through the image processing unit 25B, and an M-mode image is displayed on the display unit 7 by the display control unit 6.

The phase difference calculation unit 26 of the elasticity index calculation processing unit 5 calculates the first phase difference θ1 and the second phase difference θ2 using Equation (1) based on the phase information of the first complex data and the second complex data generated by the complex data generation unit 3. The number-of-times-of-aliasing determination unit 30 determines the number of times of aliasing N of the first phase difference using Expression (2), Equation (3), and Expression (4) based on the second phase difference calculated by the phase difference calculation unit 26. Based on the second phase difference θ2 and the number of times of aliasing N determined by the number-of-times-of-aliasing determination unit 30, the phase difference correction unit 27 corrects the first phase difference θ1.

Figure 14:
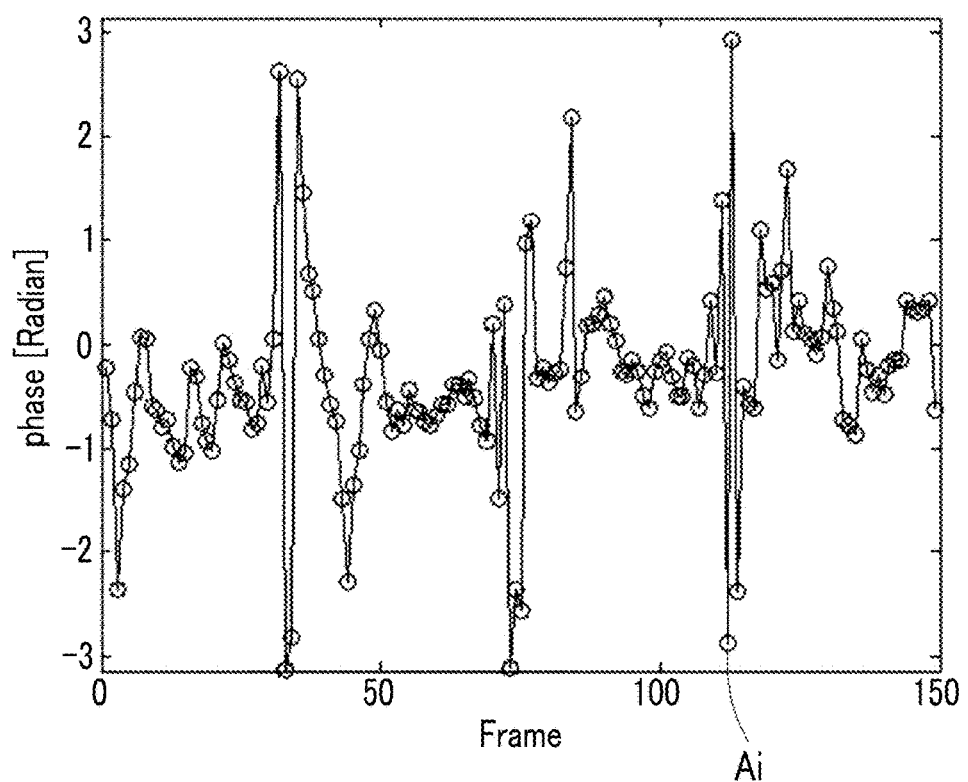
FIG. 14 is a graph showing a first phase difference at which aliasing occurs.

FIG. 14 shows an example of the first phase difference θ1 between frames calculated by the phase difference calculation unit 26 using the phase information of the first complex data obtained by using the first center frequency C1. In FIG. 14, the horizontal axis indicates a frame, and the vertical axis indicates a phase difference. Since the first complex data is obtained by using the first center frequency C1 in the high frequency region, aliasing Ai occurs at the first phase difference θ1 as shown in FIG. 14.

Figure 15:
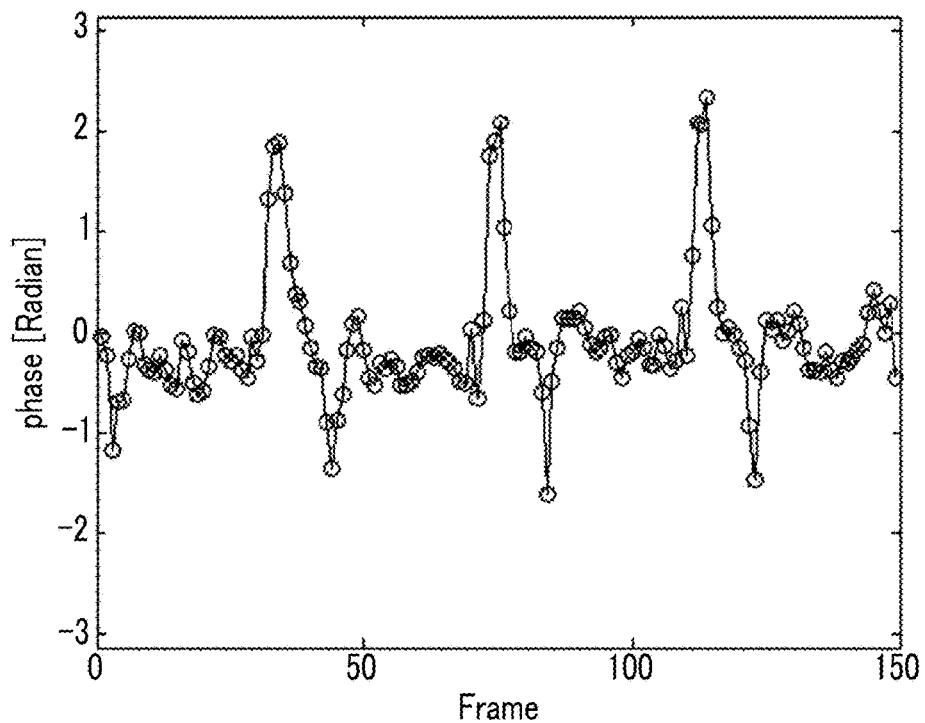
FIG. 15 is a graph showing a second phase difference at which no aliasing occurs.

On the other hand, FIG. 15 shows an example of the second phase difference θ2 between frames calculated by the phase difference calculation unit 26 using the phase information of the second complex data obtained by using the second center frequency C2. Since the second complex data is obtained by using the second center frequency C2 lower than the first center frequency C1, the robustness against aliasing noise is high. Therefore, as shown in FIG. 15, the aliasing Ai shown in FIG. 14 does not occur at the second phase difference θ2.

Figure 16:
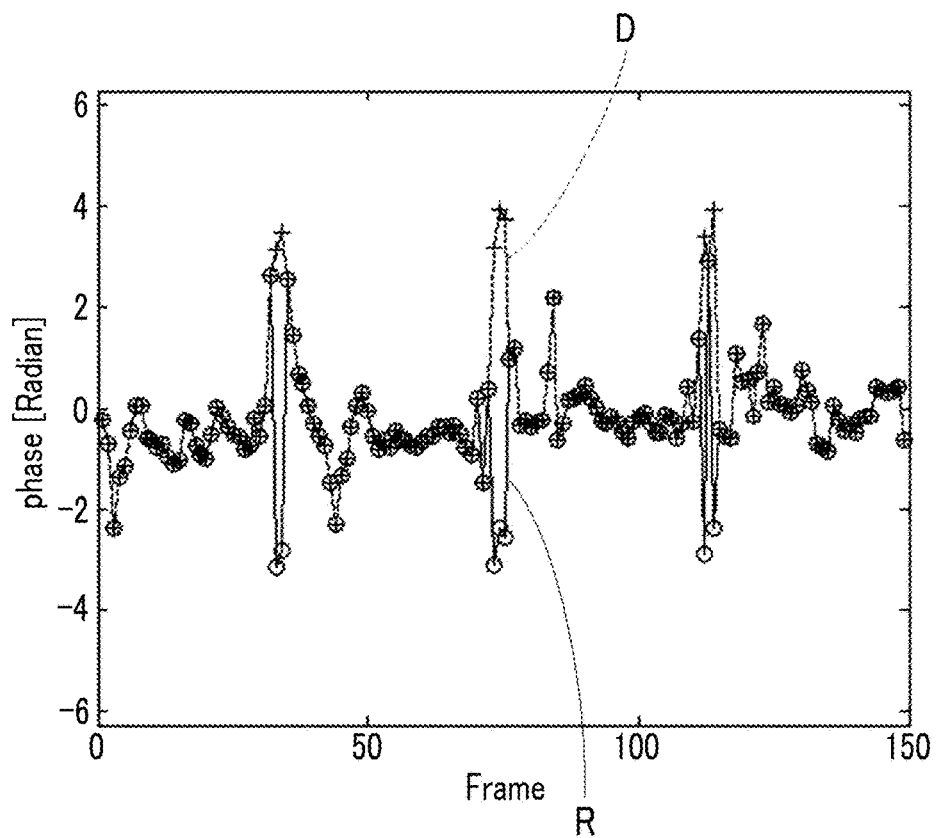
FIG. 16 is a graph showing a first phase difference after correction.

FIG. 16 shows an example in which the number-of-times-of-aliasing determination unit 30 determines the number of times of aliasing N of the first phase difference θ1 shown in FIG. 14 using Expression (2), Equation (3), and Expression (4) and the phase difference correction unit 27 corrects the first phase difference θ1 using the number of times of aliasing N and the second phase difference θ2 shown in FIG. 15. Although aliasing occurs in a waveform R before correction, aliasing is eliminated in a waveform D corrected by the phase difference correction unit 27.

Figure 17A:
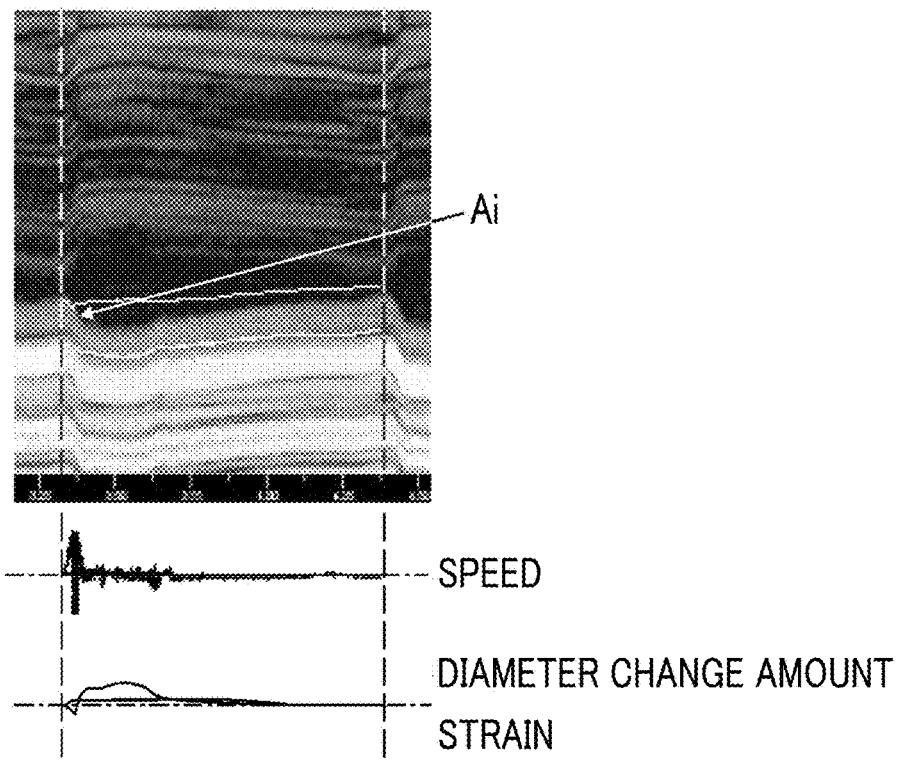
FIG. 17A is a diagram showing an example of an M-mode image in which aliasing occurs.
Figure 17B:
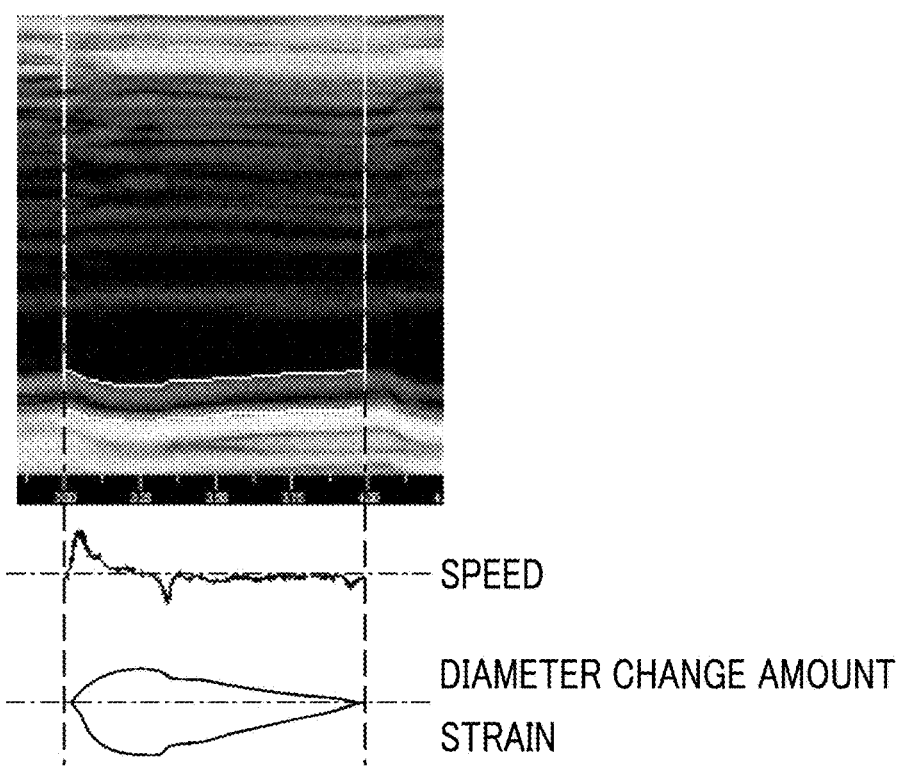
FIG. 17B is a diagram showing an example of an M-mode image in which no aliasing occurs.

The displacement amount calculation unit 28 calculates the amount of displacement of the measurement target tissue using Equations (5) and (6) based on the first phase difference θ1 corrected by the phase difference correction unit 27, and the elasticity index calculation unit 31 calculates the elasticity index of the measurement target tissue using the calculated amount of displacement. Then, as shown in FIGS. 17A and 17B, it is possible to display the movement of the measurement target tissue, which changes according to the calculated amount of displacement of the measurement target tissue, and the calculated elasticity index together with the M-mode image. In the M-mode image shown in FIGS. 17A and 17B, a white line drawn in the horizontal axis direction indicates a trajectory tracking the movement of the measurement target tissue, and a graph drawn on the lower side of the M-mode image shows the speed of the measurement target tissue and the diameter change amount and the strain that are elasticity indices.

In the case of generating an M-mode image without correcting the first phase difference θ1 at which aliasing has occurred, as shown in FIG. 17A, the aliasing Ai occurs on the M-mode image, and an error occurs in the calculated amount of displacement of the measurement target tissue. For this reason, it is difficult to accurately track the movement of the measurement target tissue. In addition, it is difficult to accurately calculate the elasticity index, such as the diameter change amount and the strain of the measurement target tissue. On the other hand, by correcting the first phase difference θ1 as described above using the phase difference correction unit 27, as shown in FIG. 17B, it is possible to accurately track the movement of the measurement target tissue without increasing the frame rate or lowering the resolution of the M-mode image. In addition, it is possible to accurately calculate the elasticity index of the measurement target tissue.

By operating the operation unit 14 by the operator, the B-mode image and the M-mode image can be collectively displayed on the display unit 7. In addition, as shown in FIGS. 17A and 17B, the elasticity indices of the measurement target tissue can also be displayed collectively.

In the case of generating the second complex data, a representative point of the measurement target tissue, for example, one or a plurality of points, such as the depth center point of the vascular wall and the point of the lumen of the blood vessel to the point of the intima boundary depth, can be set, and the first phase difference θ1 can be corrected using the second phase difference θ2 of the second complex data at the representative point.

In a case where the measurement target tissue is a blood vessel, the amount of the first phase difference θ1 in the entire region of the vascular wall using the second phase difference θ2 calculated with the vicinity of the center of the vascular wall as a representative point. In a case where measurement target tissue is an arterial wall, a thickness change (strain) is equal to or less than $\frac{1}{10}$ of the translational movement, and a change in the phase of the measurement target tissue is mostly due to the translational movement. Since the translational movement has little change in the depth direction of the measurement target tissue, the second phase difference θ2 used in determining the number of occurrences of aliasing can be calculated using only complex data at such a representative point.

By performing the detection processing and the phase difference calculation at the representative point of the measurement target tissue in this manner, it is possible to reduce the amount of calculation to about 50% compared with that in the case of calculating the phase difference for the entire measurement target tissue.

Second Embodiment

In the first embodiment described above, the transmission and reception control unit 10 of the transmission and reception unit 2 transmits and receives an ultrasound beam using one type of pulse signal. However, it is possible to transmit and receive the ultrasound beam according to a pulse inversion method using a first pulse signal and a second pulse signal that are inverted from each other.

In the second embodiment, the first complex data is calculated by orthogonally detecting the sum signal of received data corresponding to the first pulse signal and received data corresponding to the second pulse signal at the first center frequency C1 and the first cutoff frequency F1, and the second complex data is calculated by orthogonally detecting the difference signal between the received data corresponding to the first pulse signal and the received data corresponding to the second pulse signal at the second center frequency C2 and the second cutoff frequency F2.

Using such a pulse inversion method is advantageous in that nonlinear harmonic waves having a large bandwidth and high distance resolution can be obtained, the azimuth resolution becomes high since the distortion is proportional to the square of the sound pressure and accordingly side lobe artifacts can be suppressed, and echoes accumulated on the body surface can be suppressed since the amount of accumulated harmonic waves increases as the propagation distance increases. Therefore, measurement target tissue.

In a case where the pulse inversion method is used, the frame rate is halved since the first pulse signal and the second pulse signal are transmitted. In the conventional method, that is, in a case where a low-frequency ultrasound pulse and a high-frequency ultrasound pulse are transmitted respectively, the frame rate is further halved with respect to the case of using the pulse inversion method. That is, the frame rate is reduced to ¼.

However, by performing quadrature detection as described above using the first center frequency C1 and the second center frequency C2, the frame rate is halved by the pulse inversion method, but it is possible to suppress a further reduction in the frame rate.

EXPLANATION OF REFERENCES

1: ultrasound probe
1A: transducer array
2: transmission and reception unit
3: complex data generation unit
4A: B-mode processing unit
4B: M-mode processing unit
5: elasticity index calculation processing unit
6: display control unit
7: display unit
8: transmission unit
9: reception unit
10: transmission and reception control unit
11: device control unit
12: probe type detection unit
13: quadrature detection condition memory
14: operation unit
15: storage unit
16: amplification unit
17: A/D conversion unit
18: beam former
19: quadrature detection unit
20: first complex data memory
21: second complex data memory
22A, 22B: amplitude calculation unit
23A, 23B: signal processing unit
24A, 24B: DSC
25A, 25B: image processing unit
26: phase difference calculation unit
27: phase difference correction unit
28: displacement amount calculation unit
30: number-of-times-of-aliasing determination unit
31: elasticity index calculation unit
P, E: frequency band
C1: first center frequency
C2: second center frequency
F1: first cutoff frequency
F2: second cutoff frequency
θ1: first phase difference
θ2: second phase difference
α: provisional first phase difference
β: phase
A: boundary region
S: break
Ai: aliasing
D, R: waveform
N: number of times of aliasing

What is claimed is:

1. An ultrasound diagnostic apparatus, comprising:
an ultrasound probe;
a transmission and reception circuit that transmits an ultrasound beam from the ultrasound probe toward a subject, receives an ultrasound beam reflected from the subject, and processes a received signal output from the ultrasound probe to generate received data; and
a processor configured to:
generate first complex data including amplitude information and phase information by applying quadrature demodulation to the received data generated by the transmission and reception circuit using a first center frequency and a first cutoff frequency and generate second complex data by applying quadrature demodulation to the same data as the received data using a second cutoff frequency and a second center frequency lower than the first center frequency;
generate a B-mode image using amplitude information of at least one of the first complex data or the second complex data;
calculate a first phase difference between frames using phase information of the first complex data and calculate a second phase difference between frames using phase information of the second complex data;
correct the first phase difference using the second phase difference calculated from only phase information of the second complex data at one or a plurality of representative points instead of the second complex data of an entire measurement target tissue of the subject; and
calculate an amount of displacement of a measurement target tissue of the subject using the corrected first phase difference.

2. The ultrasound diagnostic apparatus according to claim 1,
wherein the first cutoff frequency is higher than the second cutoff frequency.

3. The ultrasound diagnostic apparatus according to claim 2,
wherein the processor is further configured to determine the number of times of aliasing of the first phase difference based on the second phase difference.

4. The ultrasound diagnostic apparatus according to claim 3,
wherein the processor is further configured to calculate at least one candidate for the number of times of aliasing based on the first center frequency, the second center frequency, the first cutoff frequency, and the second cutoff frequency, and determine the number of times of aliasing of the first phase difference from the at least one candidate for the number of times of aliasing.

5. The ultrasound diagnostic apparatus according to claim 4,
wherein the processor is further configured to determine whether the second phase difference is positive or negative, and set an integer part of C1/C2 as a maximum value of a candidate for the number of times of aliasing assuming that the first center frequency is C1 and the second center frequency is C2,
in a case where the second phase difference is positive, the processor is further configured to calculate at least one candidate for the number of times of aliasing satisfying $\pi \times (C2/C1) \times (2n+1) + W1 > \theta 2 \times (C2/C1) \times (2n-1) - W2$ assuming that the second phase difference is θ2, the candidate for the number of times of aliasing is n, and adjustment values each of which is set to a value of about π/4 are W1 and W2,
in a case where the second phase difference is negative, the processor is further configured to calculate at least one candidate for the number of times of aliasing satisfying $\pi \times (C2/C1) \times (2n+1) - W1 \leq \theta 2 < \pi \times (C2/C1) \times (2n-1) + W2$, and
in a case where a plurality of candidates for the number of times of aliasing are calculated, the processor is further configured to determine n at which a value of an evaluation function $\Delta e(n) = |\theta 1 + 2\pi n - (C1/C2) \times \theta 2|$ is minimized, assuming that the first phase difference is θ1, as a number of times of aliasing N of the first phase difference.

6. The ultrasound diagnostic apparatus according to claim 1, wherein the processor is further configured to determine the number of times of aliasing of the first phase difference based on the second phase difference.

7. The ultrasound diagnostic apparatus according to claim 6,
wherein the processor is further configured to calculate at least one candidate for the number of times of aliasing based on the first center frequency, the second center frequency, the first cutoff frequency, and the second cutoff frequency, and determine the number of times of aliasing of the first phase difference from the at least one candidate for the number of times of aliasing.

8. The ultrasound diagnostic apparatus according to claim 7,
wherein the processor is further configured to determine whether the second phase difference is positive or negative, and set an integer part of C1/C2 as a maximum value of a candidate for the number of times of aliasing assuming that the first center frequency is C1 and the second center frequency is C2,
in a case where the second phase difference is positive, the processor is further configured to calculate at least one candidate for the number of times of aliasing satisfying $\pi \times (C2/C1) \times (2n+1) + W1 > \theta 2 \geq \pi \times (C2/C1) \times (2n-1) - W2$ assuming that the second phase difference is $\theta 2$, the candidate for the number of times of aliasing is n, and adjustment values each of which is set to a value of about $\pi/4$ are W1 and W2,
in a case where the second phase difference is negative, the processor is further configured to calculate at least one candidate for the number of times of aliasing satisfying $\pi \times (C2/C1) \times (2n+1) - W1 \leq \theta 2 < \pi \times (C2/C1) \times (2n-1) + W2$, and
in a case where a plurality of candidates for the number of times of aliasing are calculated, the processor is further configured to determine n at which a value of an evaluation function $\Delta e(n) = |\theta 1 + 2\pi n - (C1/C2) \times \theta 2|$ is minimized, assuming that the first phase difference is $\theta 1$, as a number of times of aliasing N of the first phase difference.

9. The ultrasound diagnostic apparatus according to claim 1,
wherein the transmission and reception circuit transmits and receives an ultrasound beam according to a pulse inversion method using a first pulse signal and a second pulse signal of which phases are inverted from each other, and
the processor is further configured to generate the first complex data from a sum signal of received data corresponding to the first pulse signal and received data corresponding to the second pulse signal and generate the second complex data from a difference signal between received data corresponding to the first pulse signal and received data corresponding to the second pulse signal.

10. The ultrasound diagnostic apparatus according to claim 1, further comprising:
a quadrature detection condition memory in which a plurality of quadrature detection conditions including a first center frequency condition, a second center frequency condition, a first cutoff frequency condition, and a second cutoff frequency condition, which are set for each of a plurality of the ultrasound probes, are stored in advance; and
the processor is further configured to select the quadrature detection condition corresponding to the ultrasound probe from the plurality of quadrature detection conditions stored in the quadrature detection condition memory and generate complex data based on the quadrature detection condition.

11. The ultrasound diagnostic apparatus according to claim 1,
wherein the processor is further configured to calculate an elasticity index of the measurement target tissue using the amount of displacement of the measurement target tissue of the subject.

12. A control method of an ultrasound diagnostic apparatus, comprising:
transmitting an ultrasound beam from an ultrasound probe toward a subject, receiving an ultrasound beam reflected from the subject, and processing a received signal output from the ultrasound probe to generate received data;
generating first complex data including amplitude information and phase information by applying quadrature demodulation to the received data using a first center frequency and a first cutoff frequency and generating second complex data by applying quadrature demodulation to the same data as the received data using a second cutoff frequency and a second center frequency lower than the first center frequency;
generating a B-mode image using amplitude information of at least one of the first complex data or the second complex data;
calculating a first phase difference between frames using phase information of the first complex data and calculating a second phase difference between frames using phase information of the second complex data;
correcting the first phase difference using the second phase difference calculated from only phase information of the second complex data at one or a plurality of representative points instead of the second complex data of an entire measurement target tissue of the subject; and
calculating an amount of displacement of a measurement target tissue of the subject using the corrected first phase difference.

13. The control method of an ultrasound diagnostic apparatus according to claim 12,
wherein the first cutoff frequency is higher than the second cutoff frequency.

14. The control method of an ultrasound diagnostic apparatus according to claim 13,
wherein the number of times of aliasing of the first phase difference is determined based on the second phase difference.

15. The control method of an ultrasound diagnostic apparatus according to claim 14,
wherein at least one candidate for the number of times of aliasing is determined based on the first center frequency, the second center frequency, the first cutoff frequency, and the second cutoff frequency, and the number of times of aliasing of the first phase difference is determined from the at least one candidate for the number of times of aliasing.

16. The control method of an ultrasound diagnostic apparatus according to claim 15,
wherein whether the second phase difference is positive or negative is determined, and an integer part of C1/C2 is set as a maximum value of a candidate for the number of times of aliasing assuming that the first center frequency is C1 and the second center frequency is C2,
in a case where the second phase difference is positive, at least one candidate for the number of times of aliasing satisfying $\pi \times (C2/C1) \times (2n+1)+W1>\theta2$ $\pi \times (C2/C1) \times (2n-1)-W2$ is calculated assuming that the second phase difference is $\theta2$, the candidate for the number of times of aliasing is n, and adjustment values each of which is set to a value of about $\pi/4$ are W1 and W2, in a case where the second phase difference is negative, at least one candidate for the number of times of aliasing satisfying $\pi \times (C2/C1) \times (2n+1)-W1 \leq \theta2 < \pi \times (C2/C1) \times (2n-1)+W2$ is calculated, and in a case where a plurality of candidates for the number of times of aliasing are calculated, n at which a value of an evaluation function $\Delta e(n)=|\theta1+2\pi n-(C1/C2) \times \theta2|$ is minimized is determined, assuming that the first phase difference is $\theta1$, as a number of times of aliasing N of the first phase difference.

17. The control method of an ultrasound diagnostic apparatus according to claim 12,
   wherein the number of times of aliasing of the first phase difference is determined based on the second phase difference.

18. The control method of an ultrasound diagnostic apparatus according to claim 17,
   wherein at least one candidate for the number of times of aliasing is determined based on the first center frequency, the second center frequency, the first cutoff frequency, and the second cutoff frequency, and the number of times of aliasing of the first phase difference is determined from the at least one candidate for the number of times of aliasing.

19. The control method of an ultrasound diagnostic apparatus according to claim 18,
   wherein whether the second phase difference is positive or negative is determined, and an integer part of C1/C2 is set as a maximum value of a candidate for the number of times of aliasing assuming that the first center frequency is C1 and the second center frequency is C2, in a case where the second phase difference is positive, at least one candidate for the number of times of aliasing satisfying $\pi \times (C2/C1) \times (2n+1)+W1>\theta2 \times (C2/C1) \times (2n-1)-W2$ is calculated assuming that the second phase difference is $\theta2$, the candidate for the number of times of aliasing is n, and adjustment values each of which is set to a value of about $\pi/4$ are W1 and W2, in a case where the second phase difference is negative, at least one candidate for the number of times of aliasing satisfying $\pi \times (C2/C1) \times (2n+1)-W1 \leq \theta2 < \pi \times (C2/C1) \times (2n-1)+W2$ is calculated, and in a case where a plurality of candidates for the number of times of aliasing are calculated, n at which a value of an evaluation function $\Delta e(n)=|\theta1+2\pi n-(C1/C2) \times \theta2|$ is minimized is determined, assuming that the first phase difference is $\theta1$, as a number of times of aliasing N of the first phase difference.

* * * * *